US012805767B2

(12) United States Patent
Kawajiri et al.

(10) Patent No.: US 12,805,767 B2
(45) Date of Patent: Nov. 24, 2026

(54) BIOLOGICAL INFORMATION MEASUREMENT DEVICE

(71) Applicant: TOHOKU UNIVERSITY, Sendai (JP)

(72) Inventors: Koji Kawajiri, Chiyoda-ku (JP); Rihito Kuroda, Sendai (JP); Yasuyuki Fujihara, Sendai (JP); Shota Nakayama, Sendai (JP); Hideaki Hasegawa, Tokyo (JP); Takayori Ito, Tokyo (JP); Hiroyuki Tamaoka, Tokyo (JP)

(73) Assignee: TOHOKU UNIVERSITY, Sendai (JP)

( * ) Notice: Subject to any disclaimer, the term of this patent is extended or adjusted under 35 U.S.C. 154(b) by 472 days.

(21) Appl. No.: 18/546,372

(22) PCT Filed: Feb. 14, 2022

(86) PCT No.: PCT/JP2022/005644
§ 371 (c)(1),
(2) Date: Aug. 14, 2023

(87) PCT Pub. No.: WO2022/176802
PCT Pub. Date: Aug. 25, 2022

(65) Prior Publication Data
US 2024/0172969 A1 May 30, 2024

(30) Foreign Application Priority Data
Feb. 19, 2021 (JP) ................................ 2021-025483

(51) Int. Cl.
*A61B 5/1455* (2006.01)
*A61B 5/145* (2006.01)

(52) U.S. Cl.
CPC ........ *A61B 5/14532* (2013.01); *A61B 5/1455* (2013.01); *A61B 2562/0238* (2013.01)

(58) Field of Classification Search
CPC ... A61B 5/0059; A61B 5/0205; A61B 5/1455; A61B 5/14551; A61B 5/14552; A61B 5/14532; A61B 5/489; A61B 2560/0223
See application file for complete search history.

(56) References Cited

U.S. PATENT DOCUMENTS 5,452,716 A * 9/1995 Clift .................. A61B 5/14532 600/316
2003/0023152 A1 * 1/2003 Abbink ............... A61B 5/1455 600/316

(Continued)

FOREIGN PATENT DOCUMENTS

EP 2 901 925 A1 8/2015
EP 2 989 972 A1 3/2016

(Continued)

OTHER PUBLICATIONS

Murata et al, "A 24.3Me° Full Well Capacity CMOS Image Senser with Lateral Overflow Trench Capacitor for High Precision Near Infrared Absorption Imaging," IEDM, pp. 225-228, 2018 (Year: 2018).*

(Continued)

*Primary Examiner* — Chu Chuan Liu
(74) *Attorney, Agent, or Firm* — Oblon, McClelland, Maier & Neustadt, L.L.P.

(57) ABSTRACT

A biological information measuring device includes a light source that irradiates light, a sensor having a plurality of pixels arranged in an array in a two-dimensional plane and a saturation charge number of 1,000,000 or more. The sensor receives irradiated light transmitted, reflected, or scattered from the light source in a living body and outputs information according to the light intensity of the received light. A specific location selection unit selects a measurement target location of the measurement target for the biological information and a reference location different from the measure- (Continued)

ment target location, based on the information obtained by the image sensor. A biological information acquisition unit acquires biological information from the information obtained by the sensor at the measurement target location, using the information obtained by the sensor at the reference location as a reference.

17 Claims, 7 Drawing Sheets

(56) References Cited

U.S. PATENT DOCUMENTS

| | | | | |
|---|---|---|---|---|
| 2006/0156927 | A1* | 7/2006 | Udagawa | B01D 46/4263 96/417 |
| 2014/0024904 | A1* | 1/2014 | Takinami | A61B 5/1455 600/316 |
| 2018/0055428 | A1 | 3/2018 | Toya | |
| 2018/0344228 | A1* | 12/2018 | Yelin | A61B 5/14535 |
| 2022/0157044 | A1* | 5/2022 | Schick | G06T 7/20 |

FOREIGN PATENT DOCUMENTS

| | | | |
|---|---|---|---|
| JP | 11-244266 | A | 9/1999 |
| JP | 2018-29749 | A | 3/2018 |
| JP | 6291874 | B2 | 3/2018 |
| JP | 2019-5266 | A | 1/2019 |
| WO | 2012/049753 | A1 | 4/2012 |
| WO | WO 2012/132768 | A1 | 10/2012 |

OTHER PUBLICATIONS

International Search Report issued Apr. 26, 2022 in PCT/JP2022/005644, filed on Feb. 14, 2022, 2 pages.

Murata et al. "A 24.3Me- Full Well Capacity and High Near Infrared Sensitivity CMOS Image Sensor with Lateral Overflow Integration Trench Capacitor " Mar. 22, 2019 ITE Technical Report vol. 43, No. 11 IST2019-17, 8 pages.

Murata et al. "A High Near-Infrared Sensitivity Over 70-dB SNR CMOS Image Sensor With Lateral Overflow Integration Trench Capacitor" IEEE Transactions on Electron Devices, vol. 67, No. 4, Apr. 2020, 7 pages.

* cited by examiner

BIOLOGICAL INFORMATION MEASUREMENT DEVICE

FIELD OF THE INVENTION

The present invention relates to a biological information measurement device capable of non-invasively measuring in-vivo information (biological information).

BACKGROUND ART

Conventionally, the development of a technology for measuring biological information non-invasively without damaging the living body, particularly a technology for measuring biological information using light, is underway.

For example, Patent Document 1 as follows describes a biological information measurement device capable of causing a plurality of light emitting elements to emit light, detecting a blood vessel site based on an image received by a light receiving unit, and then selecting an irradiation location in the light emitting element and a light receiving location for measurement and a light receiving location for reference in a light receiving element. The biological information measurement device obtains the transmitted light transmitted through the blood vessel site of the measurement target and the transmitted light transmitted through the non-vascular site for reference, so that the relative transmittance of the transmitted light transmitted through the blood vessel site of the measurement target with respect to the reference transmitted light is obtained, by selecting so that the blood vessel site is located between the irradiation location and the light receiving location for measurement, and selecting so that there is no blood vessel between the irradiation location and the light receiving location for reference.

Further, for example, in Non-Patent Document 1 and Non-Patent Document 2 below describe a non-invasive blood glucose measurement using a near-infrared high-sensitivity CMOS (Complementary Metal Oxide Semiconductor) image sensor, as a means to detect the blood component concentration of the living body with high accuracy. In Non-Patent Document 1 and Non-Patent Document 2, experiments in which the glucose solution was dropped, convected, and diffused in the physiological saline in the cell was imaged by irradiating with light having a wavelength of 1050 nm, which is one of the absorption peaks of glucose, so that it is suggested that this image be used to determine glucose concentration.

CITATION LIST

Patent Literature

[Patent Document 1] Japanese Patent Publication No. 6291874

Non-Patent Literature

[Non-Patent Document 1] "A 24.3Me-Full Well Capacity and High Near Infrared Sensitivity CMOS Image Sensor with Lateral Overflow Integration Trench Capacitor" Mar. 22, 2019 ITE Technical Report Vol. 43, No. 11 IST2019-17 (March 2019)

[Non-Patent Document 2] "A High Near-Infrared Sensitivity Over 70-dB SNR CMOS Image Sensor With Lateral Overflow Integration Trench Capacitor" IEEE TRANSACTIONS ON ELECTRON DEVICES, VOL. 67, NO. 4, APRIL 2020

SUMMARY OF THE INVENTION

Technical Problem

In the disclosed technology of Patent Document 1, when visualizing blood vessels in a living body and measuring glucose concentration (blood glucose) in the blood, the transmitted light of the blood vessel site is acquired and the transmitted light of a non-vascular region is acquired as a reference. However, it is necessary to first detect the blood vessel position in the blood vessel pattern acquisition stage, using all the light emitting elements and the light receiving elements, and then thereafter in the measurement stage, the light emitting elements and the light receiving elements must be selected based on the blood vessel position and the non-vascular region detected in the blood vessel pattern acquisition stage. This means that it is necessary to emit light and receive light in a plurality of stages including the blood vessel pattern acquisition stage and the measurement stage. When light emission and light reception are performed in a plurality of stages in this way, a time lag occurs between the blood vessel pattern acquisition stage and the measurement stage. Therefore, for example, there is a problem that the movement of the subject may cause a misalignment between the blood vessel position and the non-vascular region in the measurement stage, so that the accuracy of the reference is lowered.

Further, in the technology described in Patent Document 1, it is necessary to select the irradiation position in the light emitting element, the light receiving position for measurement and the light receiving position for reference in the light receiving element in the measurement stage, and in particular, it is necessary to store the light emitting range corresponding to the irradiation position and to selectively cause only the light emitting element located in the range to emit. As described above, in the technology described in Patent Document 1, since it is necessary to introduce a control unit for selectively operate the light emitting element and the light receiving element, there is also a problem that the device becomes complicated and the cost required for development and introduction increases.

Further, in Non-Patent Document 1 and Non-Patent Document 2, although the glucose solution in the cell is imaged, specific measurement methods and measuring instruments for actually measuring the blood glucose in the living body in a non-invasive manner are not described.

The present invention has been made in view of the above problems, and it is the object of the present invention to provide a biological information measurement device capable of measuring the biological information by acquiring both of the information for obtaining the biological information of the measurement target and a highly accurate reference by one light emission and light reception without requiring light emission and light reception in a plurality of stages.

MEANS TO SOLVE PROBLEMS

As a result of diligent research in view of the above problems, the present inventors found out that a highly accurate reference can be acquired by one light emission and light reception without requiring light emission and light reception in a plurality of stages, by using a sensor having a saturation charge number is not smaller than a specific number.

More specifically, the present inventors found out that it is possible to properly image both the measurement target location and the reference location by emitting and receiving light once, by using a sensor with a saturation charge amount of 1,000,000 or more, with the result that both the information for obtaining the biological information of the measurement target and the highly accurate reference can be acquired at one time.

The biological information measurement device according to the present invention comprises: a light source that irradiates light; an image sensor that receives the light irradiated from the light source transmitted, reflected or scattered in a living body, outputs information according to the amount of the received light, has a plurality of pixels arranged in an array in a two-dimensional plane, and has a saturation charge number of 1,000,000 or more; a specific location selection unit that selects a measurement target location of the measurement target for the biological information and a reference location different from the measurement target location, based on the information obtained by the image sensor; and a biological information acquisition unit that acquires the biological information from the information obtained by the image sensor at the measurement target location by using the information obtained by the image sensor at the reference location as a reference.

According to the above configuration, it is possible to provide a biological information measurement device capable of measuring the biological information by acquiring both of the information for obtaining the biological information of the measurement target and a highly accurate reference by single light emission and light reception without requiring light emission and light reception in multiple stages.

In the biological information measurement device according to the present invention, an SN ratio of the image sensor may be 60 dB or more.

According to the above configuration, it is possible to provide a biological information measurement device capable of measuring the biological information by acquiring both of the information for obtaining the biological information of the measurement target and a highly accurate reference by single light emission and light reception without requiring light emission and light reception in multiple stages.

In the biological information measurement device according to the present invention, the light source may be a surface emitting type light emitting diode.

According to the above configuration, the light source can irradiate uniform and even light on a surface perpendicular to the light irradiation direction to improve the accuracy of the reference.

In the biological information measurement device according to the present invention, an in-plane variation of the surface emitting type light emitting diode may be 10% or less.

According to the above configuration, the light source can more reliably irradiate uniform and even light on a surface perpendicular to the light irradiation direction.

In the biological information measurement device according to the present invention, an optical element having a transverse mode conversion function may be arranged between the light source and the image sensor.

According to the above configuration, the light irradiated from the light source can be converted into uniform and even light on the plane perpendicular to the light irradiation direction.

In the biological information measurement device according to the present invention, the optical element may be an aspherical lens.

According to the above configuration, the light irradiated from the light source can be reliably converted into light that is uniform and even on the plane perpendicular to the light irradiation direction.

In the biological information measurement device according to the present invention, the optical element may be a diffractive optical element.

According to the above configuration, the light irradiated from the light source can be reliably converted into light that is uniform and even on the plane perpendicular to the light irradiation direction.

In the biological information measurement device according to the present invention, the optical element may be a parallel flat plate of quartz.

According to the above configuration, the light irradiated from the light source can be reliably converted into light that is uniform and even on the plane perpendicular to the light irradiation direction.

In the biological information measurement device according to the present invention, the specific location selection unit may select a portion including the biological information of the measurement target as the measurement target location and select a location that does not include thee biological information of the measurement target as the reference location, in the two-dimensional image information formed from the information obtained by the image sensor.

According to the above configuration, the measurement target location and the reference location can be selected based on the two-dimensional image information captured by the image sensor.

In the biological information measurement device according to the present invention, the measurement target location may be a location including a blood vessel in the living body, and the reference location may be a location not including the blood vessel in the living body.

According to the above configuration, the information outside the blood vessel can be used as a reference when acquiring the biological information contained in the blood inside the blood vessel.

In the biological information measurement device according to the present invention, the biological information may be a blood glucose in the blood in the living body.

According to the above configuration, it is possible to provide a biological information measurement device capable of measuring the blood glucose in the blood in the living body.

DETAILED DESCRIPTION OF EMBODIMENTS

Hereinafter, the embodiment of the biological information measurement device according to the present invention will be described with reference to the drawings.

The biological information measurement device according to the present invention comprises: a light source that irradiates light; an image sensor that receives light emitted from the light source transmitted, reflected or scattered in a living body, outputs information according to the amount of the received light, has a plurality of pixels arranged in an array in a two-dimensional plane, and has a saturation charge number of 1,000,000 or more; a specific location selection unit that selects a measurement target location of the measurement target for the biological information and a reference location different from the measurement target location based on the information obtained by the image sensor; and a biological information acquisition unit that acquires biological information from the information obtained from the image sensor at the measurement target location by using the information obtained from the image sensor at the reference location as a reference.

Figure 1:
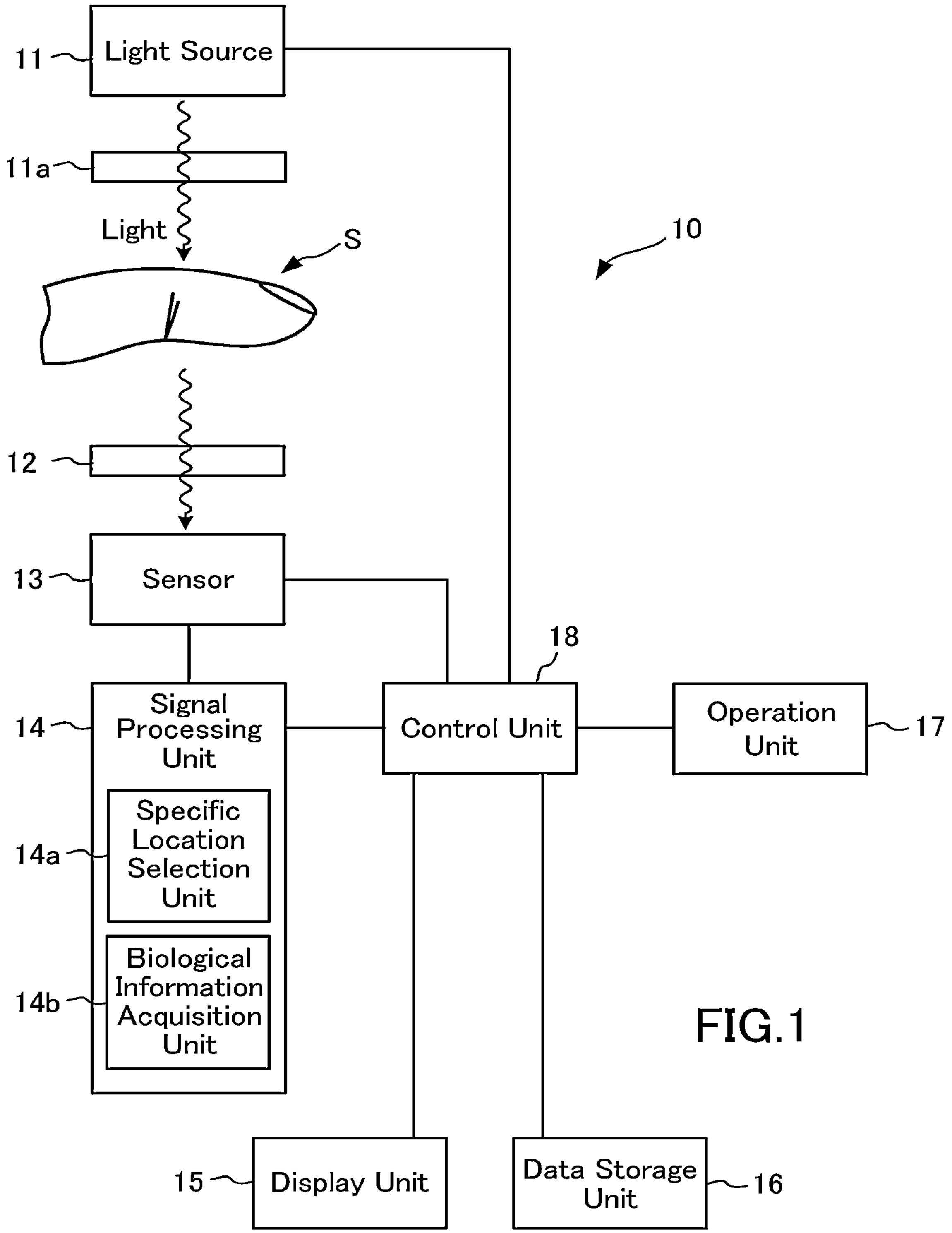
FIG. 1 is a block diagram showing an example of the configuration of a biological information measurement device according to an embodiment of the present invention.

The configuration of the biological information measurement device in the present embodiment will be described. FIG. 1 is a block diagram showing an example of the configuration of the biological information measurement device according to the present embodiment.

The biological information measurement device 10 shown in FIG. 1 is constituted by a light source 11, an optical element 11*a*, a filter 12, a sensor 13, a signal processing unit 14, a display unit 15, a data storage unit 16, an operation unit 17, and a control unit 18.

The light source 11 is a device that emits light used for measuring biological information (for example, the blood glucose of blood in the living body). In the present invention, the reference signal acquired at the reference location is used to acquire biological information from the information acquired at the measurement target location. At this time, if the reference superimposed on the information acquired at the measurement target location and the reference acquired at the reference location are significantly different from each other, it may not be possible to appropriately acquire highly accurate biological information. Therefore, it is preferable that the sensor 13 can receive light from the light source 11 under the same conditions at an arbitrary position (arbitrary pixel portion) on the light receiving surface. In order to realize this, the light source 11 is preferably capable of irradiating uniform and even light on a surface perpendicular to the light irradiation direction, and is preferably a surface emitting type light emitting diode, for example. The surface light emitting diode referred to here also includes a laser diode having a reflecting mirror formed on both end faces or one end face. In the case of a surface light emitting diode, a single diode chip can relatively easily form a wide and uniform light distribution, which is preferable for this application. On the other hand, since the light distribution emitted from each chip of the end face light emitting diode is limited to a narrow range, it is necessary to arrange the chips in an array in order to form a wide light distribution. Further, the light source 11 in the present embodiment is preferably capable of irradiating a high amount of light (high illuminance), and for example, a surface emitting type light emitting diode having a maximum output of about 1 W may be used. Further, the light source 11 may be configured to switch a plurality of light wavelengths.

Further, in order to further improve the accuracy of surface emission, an optical element 11*a* having a transverse mode conversion function may be provided. The optical element 11*a* has a function of converting the light distribution (transverse mode) in the surface of the surface emission emitted by the surface emission type light emitting diode so as to have a more uniform and even distribution. The optical element 11*a* is not particularly limited, but for example, an aspherical lens, a diffractive optical element, a quartz parallel flat plate, or the like can be used.

In the biological information measurement device 10 of the present embodiment, the irradiation direction of the light emitted by the light source 11 at the time of measuring the biological information (when the optical element 11*a* is provided, the light converted to the transverse mode by the optical element 11*a*), the subject S, which is a living body, is arranged. The light irradiated to the subject S is transmitted, reflected, or scattered in the subject S.

The sensor 13 is arranged in the subject S at a position where it can receive the transmitted, reflected, or scattered light. The sensor 13 has a function of outputting an electric signal corresponding to the received light. For example, a CMOS image sensor capable of outputting an electric signal that can be finally processed as image information from the received light can be used as the sensor 13. The CMOS image sensor applicable to the present invention preferably satisfies a specific condition, and the details thereof will be described later.

A filter 12 that transmits only light having a specific wavelength may be provided in front of the light receiving portion of the sensor 13. The wavelength of the light transmitted through the filter 12 can be appropriately determined according to the characteristics of the biological information of the measurement target. For example, when the light source 11 is configured to emit light having a single wavelength, only light having the same wavelength as the light emitted by the light source 11 may be configured to reach the sensor 13 at the subsequent stage by providing a filter 12 that transmits only light having the same wavelength as the light emitted by the light source 11. Further, in order to further narrow down the light wavelength, the transmission characteristic of the filter 12 may be adjusted so that only the light having a part of the wavelength band included in the light emitted by the light source 11 reaches.

The signal processing unit 14 is configured to perform processing related to the information outputted from the sensor 13. The signal processing unit 14 has a function of performing image processing based on the information output from the sensor 13 and a function of outputting the image information to the display unit 15 and the data storage unit 16.

The signal processing unit 14 has a specific location selection unit 14*a* and a biological information acquisition unit 14*b*.

The specific location selection unit 14*a* has a function of selecting a measurement target location of the measurement target and a reference location different from the measurement target location of the biological information of the subject S based on the information obtained by the sensor 13. More specifically, the specific location selection unit 14*a* has a function of selecting an image region including biological information as a measurement target in the image information formed based on the information outputted by the sensor 13, and a function of selecting an image region that does not contain certain biological information that is the measurement target as a reference location. As an example, when the biological information of the measurement target is the blood glucose in the blood in the living body, the specific location selection unit 14*a* selects an image region including a blood vessel site in the living body as the measurement target location from the image information, and selects an image region that does not include a blood vessel site in the living body as a reference site.

The method of selecting the measurement target location and the reference location by the specific location selection unit 14*a* is not particularly limited, and for example, an image region containing biological information and an image region not including biological information are identified by performing image information analysis processing. Alternatively, the user may refer to the image information displayed on the display unit 15, and use the operation unit 17 to select an image region containing biological information and an image region not including biological information.

The specific location selection unit 14*a* can select the measurement target location and the reference location from one image information, but the measurement target location and the reference location can be selected based on a plurality of image information (a plurality of frames constituting the video). For example, the specific location selection unit 14*a* may tentatively select a measurement target location and a reference location from each of a plurality of image information, and determine the frequently selected location as the measurement target location and the reference location. Further, the specific point selection unit 14*a* may select a plurality of measurement target locations and a plurality of reference locations in one image information.

The biological information acquisition unit 14*b* has a function of using the information obtained by the sensor 13 at the reference location as a reference and acquiring biological information from the information obtained by the sensor 13 at the measurement target location. For example, the biological information acquisition unit 14*b* can use the light receiving amount of the sensor 13 included in the reference location as a reference, calibrate the light receiving amount of the sensor 13 included in the measurement target location by the reference, and acquire biological information from the amount of light received at the measurement target location calibrated using the reference in the image information formed on the basis of information output by the sensor 13.

The method of calibrating the light receiving amount of the sensor 13 included in the measurement target location by the reference is not particularly limited. For example, the accurate amount of light irradiated to the measurement target location may be calculated, by performing an arithmetic calculation from the amount of light received at the measurement target location, considering the reference locations that do not include the measurement target of the biological information as an influence of the background, by calculating the reference transmittance from the amount of light received at the reference location and calibrating the amount of light received at the measurement target location using the reference transmittance.

The method of acquiring biological information from the light receiving amount of the calibrated measurement target location obtained by the calibrating using the reference is not particularly limited, and for example, the biological information may be specified by preliminarily determining a calibration curve representing the relationship between the amount of light received and the biological information obtained by sensor 13, and identifying the biological information from the amount of light received at the measurement target location after the calibration, with reference to the calibration curve.

The biological information acquisition unit 14*b* can acquire biological information such as the blood glucose of the subject S from one image information, but the biological information acquisition unit 14*b* may alternatively acquire the glucose level of the subject S based on a plurality of image information (a plurality of frames constituting the image). For example, the biological information acquisition unit 14*b* may acquire biological information such as a blood glucose from each of a plurality of image information and calculate an average value or a median value thereof.

The signal processing unit 14 has a function of outputting the biological information acquired by the biological information acquisition unit 14*b* to the display unit 15 and the data storage unit 16 in the same manner as the output of the image information.

The signal processing unit 14 can be realized by a processor that performs digital signal processing. An AFE (analog front end) board that adjusts the analog signal output from the sensor 13 and converts it into a digital signal and outputs the signal may be provided between the sensor 13 and the signal processing unit 14. Further, an analog-to-digital conversion circuit may be provided in the sensor 13 to output a digital signal from the sensor 13.

The display unit 15 is constituted by a monitor such as a liquid crystal display or an organic EL display, and has a function of displaying image information processed by the signal processing unit 14 and biological information calculated by the signal processing unit 14 as visual information.

The data storage unit 16 is an auxiliary storage device such as an HDD (hard disk) or SSD (solid state disk), and has a function of storing image information and biological information. Various data stored in the data storage unit 16 can be read out after the fact, and can be displayed on the display unit 15 at a desired timing or transferred to another device via a data transfer unit (not shown). The communication means at the time of data transfer may be either wired or wireless.

The operation unit 17 has a function of receiving an operation instruction from the user to the biological information measurement device 10. The operation unit 17 is an operation input device such as a mouse or a keyboard used by the user to input an operation instruction.

The control unit 18 has a function of controlling the operation of the biological information measurement device 10. As an example, the control unit 18 is connected to a light source 11, a sensor 13, a signal processing unit 14, a display unit 15, a data storage unit 16, and an operation unit 17. The control unit 18 has a function of realizing an appropriate operation in the biological information measurement device 10 by controlling the processing in each component unit.

The control unit 18 can be realized by a processor having a function of performing digital signal processing in the same manner as the signal processing unit 14. The signal processing unit 14 and the control unit 18 may be realized by different processors or may be realized by the same processor. The operation control in the biological information measurement device 10 is realized, for example, by preparing a program described to perform a desired operation and appropriately executing the program in the signal processing unit 14 and the control unit 18.

Further, a part of the biological information measurement device 10 may be configured by a computer such as a personal computer. In this case, the signal processing unit 14 and the control unit 18 can be realized by a CPU that executes a program described to perform a desired operation. The display unit 15, the data storage unit 16, and the operation unit 17 can be realized by a monitor connected to a computer, an auxiliary storage device such as an HDD, a mouse, a keyboard, or the like, respectively.

As long as the light emitted by the light source 11 is irradiated to the subject S and the sensor 13 is configured to receive the light transmitted, reflected, or scattered in the subject S, the arrangement positions of the light source 11, the subject S and the sensor 13 are not particularly limited. For example, as schematically shown in FIG. 1, the sensor 13 may be arranged in the irradiation direction of the light emitted by the light source 11, and the sensor 13 may directly receive the transmitted light transmitted through the subject S. Alternatively, the sensor 13 may be arranged at a position where the sensor 13 does not directly receive the light transmitted through the subject S, and the sensor 13 may mainly receive the reflected light or the scattered light from the subject S.

The subject S may be a part of the subject's living body, and for example, the subject's fingers, wrists, arms, and the like can be used as the measurement site. The biological information of the measurement target by the biological information measurement device 10 is not particularly limited, and is configured so that the biological information can be analyzed from the image information acquired by the imaging by imaging an arbitrary part in the living body. The biological information measurement device 10 may be a wearable terminal that can be worn by the subject.

The biological information that can be measured by the biological information measurement device 10 in the present embodiment is not particularly limited, but for example, the blood glucose in the blood in the living body, oxygen saturation, hemoglobin concentration, hematocrit value, pulse, blood flow rate, cholesterol concentration and the like can be the measurement target.

Next, the sensor 13 will be described. As the sensor 13 in the present embodiment, for example, the CMOS image sensors described in Non-Patent Document 1 and Non-Patent Document 2 can be preferably used. The disclosures of Non-Patent Document 1 and Non-Patent Document 2 are incorporated herein by reference.

Non-Patent Document 1 and Non-Patent Document 2 describe CMOS image sensors in which a horizontal overflow accumulation trench capacity is mounted on each pixel on a p-type Si substrate having a low impurity concentration in which the impurity concentration is reduced to about $10^{12}$ $cm^{-3}$, and a high number of saturated electrons (>10 million) with high quantum efficiency in the near-infrared region is combined. This CMOS image sensor achieves a linear response to light from low to high illuminance, a saturation charge number of 24,300,000, a signal-to-noise ratio (SN ratio) of 71.3 dB, and high quantum efficiency in the wide light wavelength band of 200 to 1100 nm.

Hereinafter, the outline and features of the CMOS image sensors described in Non-Patent Document 1 and Non-Patent Document 2 will be described with reference to FIGS. 2 to 4.

Figure 2:
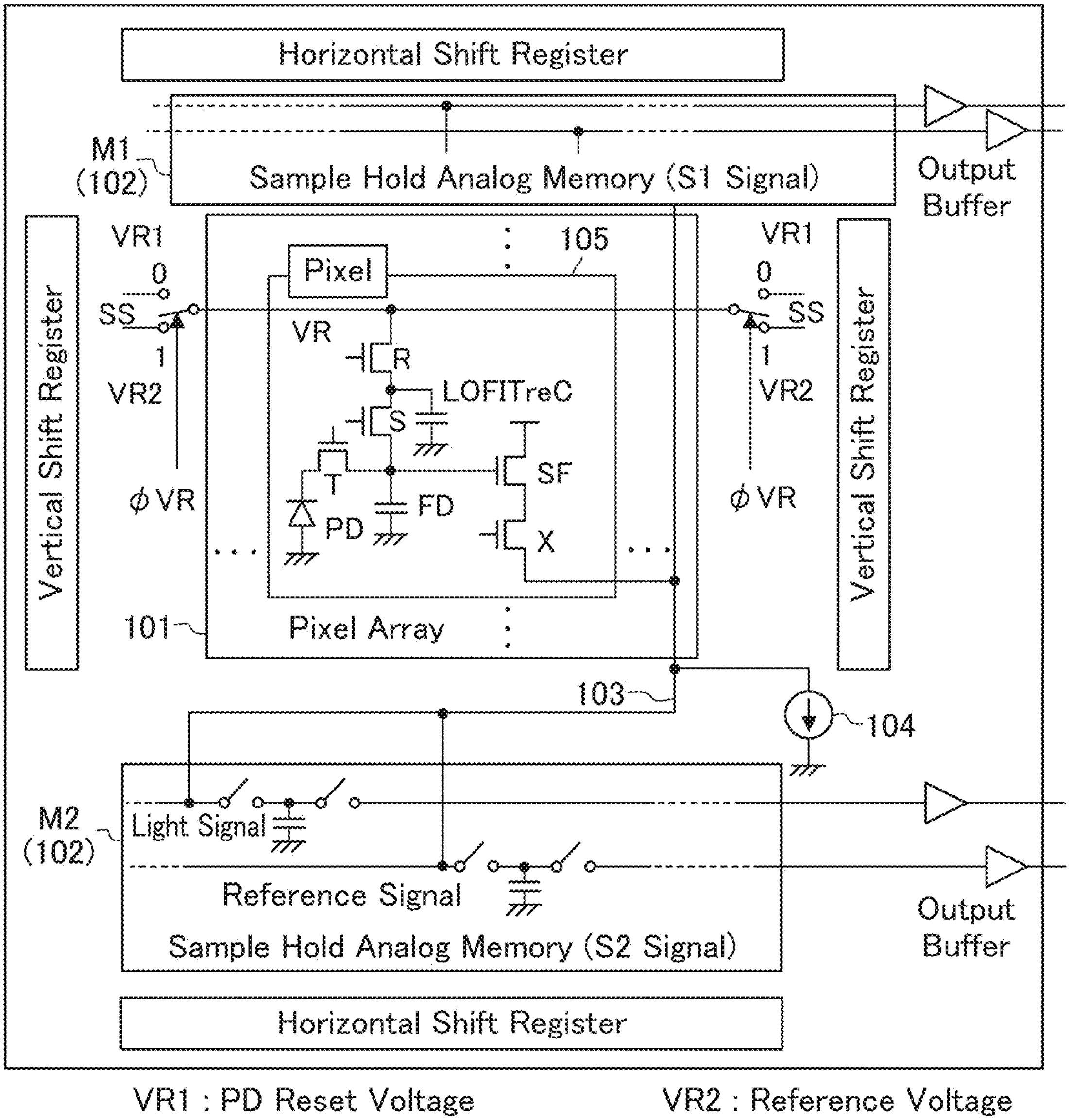
FIG.2 (PRIOR ART)
FIG. 2 is a diagram showing an example of an optical sensor unit of a CMOS image sensor that can be preferably used in the embodiment of the present invention.

FIG. 2 is a diagram showing an example of an optical sensor unit of a CMOS image sensor that can be suitably used in the present embodiment. FIG. 2 schematically shows an equivalent circuit diagram including a pixel circuit and a read circuit for one row as a part of the optical sensor unit of the CMOS image sensor.

The optical sensor unit of the CMOS image sensor shown in FIG. 2 is constituted by a pixel array unit 101 and a reading unit 102 including sample hold analog memories M1 and M2. The pixels 105 included in the pixel array unit 101 and the reading unit 102 are electrically connected to each other through the pixel train output signal line 103. A current source 104 composed of, for example, a MOS transistor is connected to the pixel train output signal line 103.

Pixel 105 is constituted by an embedded completely depleted photodiode PD, that generates an optical charge according to the intensity of light, a transfer gate T that transfers the optical charge from the photodiode PD, a floating diffusion capacitance FD in which the optical charge is transferred through the transfer gate T, a horizontal overflow storage trench capacity LOFITreC which stores the optical charge overflowing from the photodiode PD during the optical charge storage operation, a connection switch S that electrically couples or divides the floating diffusion capacitance FD and the horizontal overflow storage trench capacity LOFITreC, a reset gate R for discharging the optical charge inside the horizontal overflow storage trench capacity LOFITreC and floating diffusion capacitance FD which is formed to connect directly to the horizontal overflow storage trench capacitance LOFITreC and to the floating diffusion capacitance FD via connection switch S, a source follower amplifier SF that amplifies and converts the optical charge in the horizontal overflow storage trench capacity LOFITreC and floating diffusion capacitance FD into a voltage signal, and a pixel selection switch X for pixel selection formed to connect to the source follower amplifier SF.

In the optical sensor unit of the CMOS image sensor, a plurality of pixels 105 having the above configuration are arranged in an array in a two-dimensional plane. At both ends of the pixel array section 101, in which 105 pixels are arranged in array form, a selection switch SS is provided to control the voltage of the drive line connected to the gate electrode of the reset gate R. The system is configured so that either the PD reset voltage VR1 or the reference voltage VR2 can be selected by switching the selection switch SS with the selection pulse φVR.

Sample hold analog memories M1 and M2 are connected to the pixel train output signal line 103.

The sample hold analog memory M1 is a train circuit unit that outputs a voltage signal in which the optical charge transferred into the floating diffusion capacitance FD is converted. The sample hold analog memory M1 is configured to output a reference signal including thermal noise taken in when the floating diffusion capacitance FD is reset to a predetermined voltage and a voltage signal in which a voltage signal based on the amount of optical charge is superimposed on the thermal noise, to remove the fixed pattern noise and thermal noise caused by variation in the characteristics of the source follower amplifier SF due to the operating amplifier outside the pixel chip, so that a high-sensitivity signal S1 that captures light emission under low illuminance can be obtained.

On the other hand, the sample hold analog memory M2 is a train circuit unit that outputs a voltage signal in which the optical charge transferred to the horizontal overflow storage trench capacity LOFITreC and the floating diffusion capacitance FD is converted. The sample hold analog memory M2 is configured to output a voltage signal and a reset level signal based on the amount of light charge, to remove the fixed pattern noise and thermal noise caused by variation in the characteristics of the source follower amplifier SF due to the operating amplifier outside the pixel chip, so that a high saturation signal S2 that captures light emission under high emission can be obtained.

Furthermore, the sample hold analog memory M2 is configured to outputs a high saturation signal S2 indicating the difference between the signal voltage level after the storage period and the reference voltage VR2, by setting the voltage level of the reference voltage VR2, which is switched by the selection switch SS as described above, to an intermediate value between the saturation level and the signal level. And M2 is configured to be able to output a high saturation signal S2 capable of capturing a minute change in the amount of light under high illuminance with high accuracy, by amplifying the signal using a gain amplifier or the like in the signal readout circuit in the subsequent stage.

The optical sensor unit of the CMOS image sensor shown in FIG. 2 can operate in two operation modes, which are an operation mode that supports a wide dynamic range (LOFIC operation mode), and an operation mode that can capture changes in the amount of light in the high illuminance region (Dual VR operation mode). In the LOFIC operation mode, the optical sensor unit of the CMOS image sensor can output the above-mentioned high-sensitivity signal S1 and high-saturation signal S2, can achieve a wide dynamic range with a single exposure, and is adaptable to luminescence imaging, which captures minute luminescence in low light conditions, and to imaging targets with large differences in brightness and darkness. On the other hand, in the Dual VR operation mode, the optical sensor portion of the CMOS image sensor is specialized for, for example, absorption imaging under high emittance, and it is possible to clearly capture minute changes in the amount of light even under high emittance.

Figure 3:
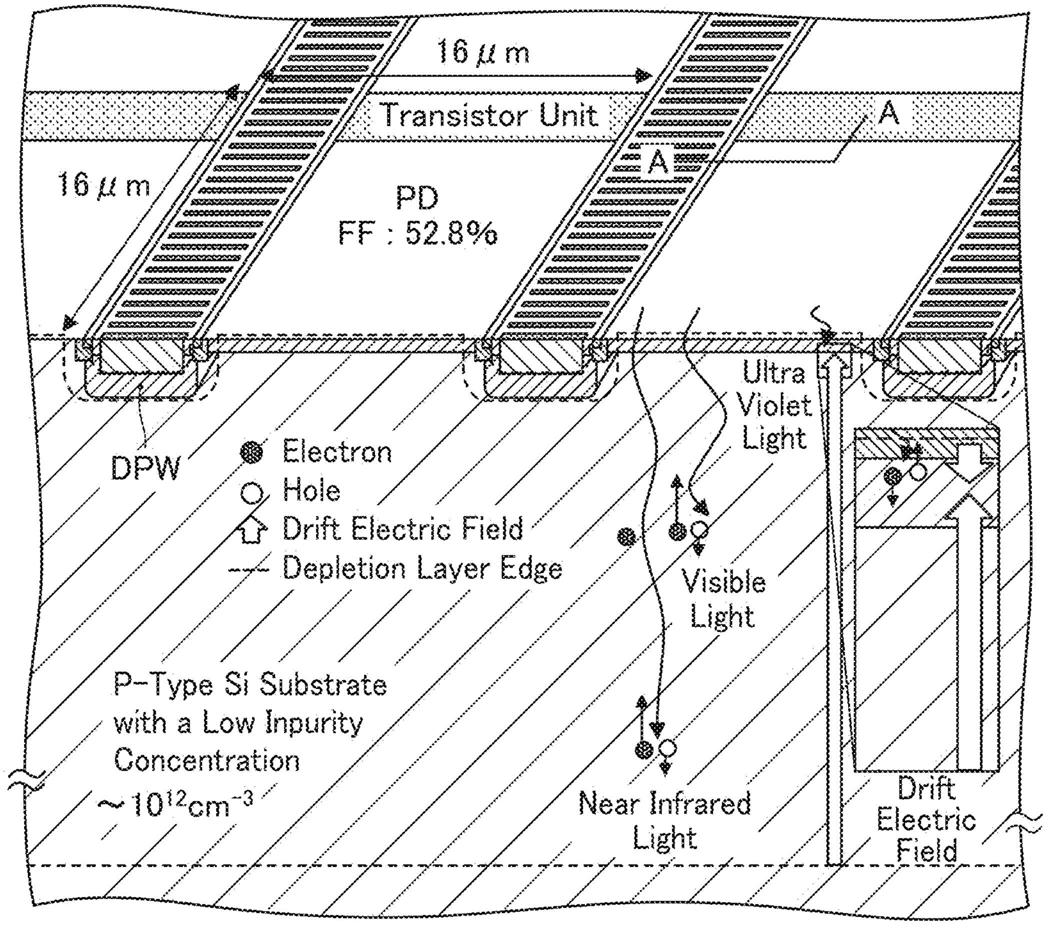
FIG.3 (PRIOR ART)
FIG. 3 is a schematic pixel cross-sectional view of a CMOS image sensor that can be preferably used in the embodiment of the present invention, and is a schematic cross-sectional view showing a cross section of a pixel array.

FIG. 3 is a schematic pixel cross-sectional view of a CMOS image sensor that can be suitably used in the present embodiment, and is a schematic cross-sectional view showing a cross section of a pixel array. Further, FIG. 4 is a cross-sectional view taken along the line A-A of FIG. 3, which is a schematic enlarged cross-sectional view of a pixel in and around the photodiode.

Figure 4:
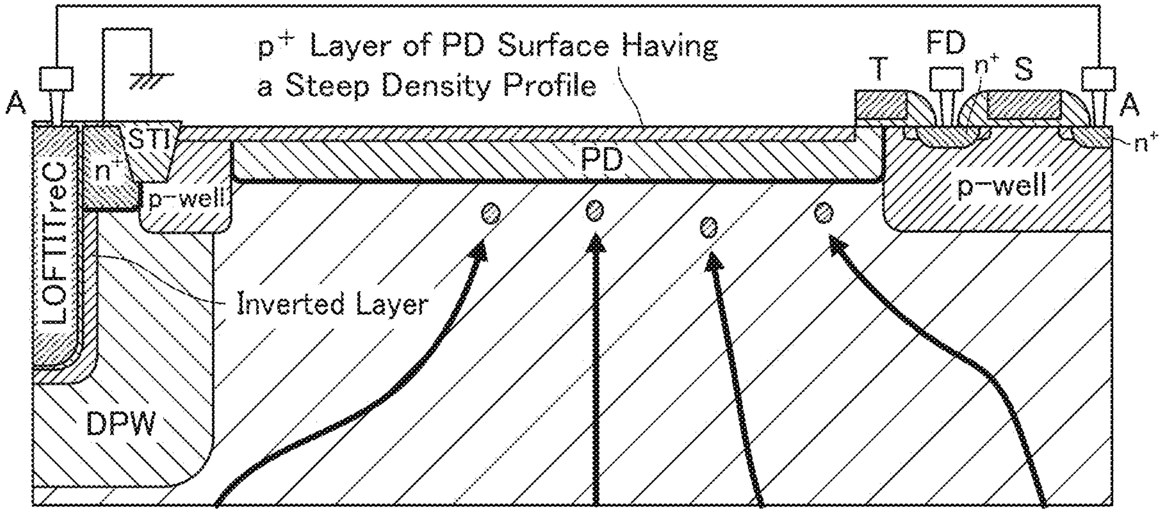
FIG.4 (PRIOR ART)
FIG. 4 is a cross-sectional view taken along the line A-A of FIG. 3, which is a schematic enlarged cross-sectional view of a pixel in and around the photodiode.

For the CMOS image sensor shown in FIGS. 3 and 4, a low impurity concentration p-type Si substrate (high resistance substrate) made of a wafer having a low impurity concentration and an extremely low oxygen concentration manufactured by the Cz (Czochralski) method is used. The CMOS image sensor is manufactured, for example, by a process of forming STI (shallow trench isolation) which is an element separation region, forming a horizontal overflow storage trench capacitance LOFITreC, forming a transistor portion and a photodiode, and forming a metal wiring.

This CMOS image sensor achieves high quantum efficiency in the wide light wavelength band of 200 to 1100 nm. This CMOS image sensor adopts a surface irradiation structure so that near-infrared light with a long wavelength does not affect the operation of the transistor in the pixel, and in addition, in order to achieve both high sensitivity and high light resistance to ultraviolet light, a $p^+$ layer having a steep density profile is formed on the surface of the photodiode PD as shown in FIG. 4.

As shown in FIG. 3, a photodiode PD and a transistor portion are arranged on the surface of the Si substrate to form a pixel array. As an example, the size of the pixel array is 2.1 mm in the horizontal direction×2.1 mm in the vertical direction, the number of pixels is 128 in the horizontal direction×128 in the vertical direction, the pixel size is 16 μm in the horizontal direction×16 μm in the vertical direction, and the opening ratio is 52.8%. Further, a horizontal overflow storage trench capacity LOFITreC is provided in each pixel. The horizontal overflow storage trench capacity LOFITreC is a capacitor containing a three-dimensional structure, and it is composed of a trench (shallow groove) formed in the pixel of the Si substrate, an oxide film formed along the trench, and a doped poly-Si electrode node embedded in the trench. By accumulating the trench capacity at a high density as the horizontal overflow storage trench capacity LOFITreC, the saturation charge number can be increased so that the opening ratio can be improved.

Leakage current may occur between the embedded n-type layer of the photodiode PD and the inverted layer induced by the horizontal overflow storage trench capacity LOFITreC. As shown in FIG. 4, a deep p-well (DPW) is formed so as to cover the entire surface of the horizontal overflow storage trench capacity LOFITreC in order to suppress the generation of leakage current while maintaining the opening ratio. The concentration of DPW is optimized so as to be able to obtain a uniform capacitance over the signal voltage range of the horizontal overflow storage trench capacitance LOFITreC (For example, 0.5-3.0 V). Further, in order to keep the leak current from the charge storage node of the horizontal overflow storage trench capacity LOFITreC low, the CMOS image sensor is so configured that the charge overflowing from the photodiode PD and the floating diffusion capacitance FD is stored in the electrode node in the horizontal overflow storage trench capacity LOFITreC.

Further, near-infrared light has a large penetration depth from the surface of the photodiode PD, so that, in order to detect near-infrared light, it is necessary to accumulate and detect the optical charge photoelectrically converted in the deep portion of the photodiode PD. In order to drift the light charge due to the near-infrared light generated in the deep part of the photodiode PD to the photodiode PD, in this CMOS image sensor, a potential gradient is formed in the p-well and DPW under the region of the transistor portion. Further, the inverted layer and the n+ layer induced at the Si substrate side interface of the horizontal overflow storage trench capacity LOFITreC are connected to the ground (GND).

Further, a negative potential (for example, a potential of about 3.0 V at maximum) may be applied to the back surface side (lower side of FIGS. 3 and 4) of the Si substrate to form an electric field in the depth direction of the Si substrate. Alternatively, the thickness of the Si substrate may be reduced. As a result, it is possible to suppress interpixel crosstalk of light charges due to the charge diffusion effect during drift for near-infrared light having a large penetration length, and improve the sensitivity and resolution of near-infrared light.

The CMOS image sensor described above with reference to FIGS. 2 to 4 describes the CMOS image sensor described in Non-Patent Document 1 and Non-Patent Document 2. In the present invention, the CMOS image sensors described in Non-Patent Document 1 and Non-Patent Document 2 can be preferably used. However, the present invention is not limited to the use of the CMOS image sensor described in Non-Patent Document 1 and Non-Patent Document 2, and for example, a sensor satisfying the specific conditions listed below can be applied to the present invention.

The sensor 13 applicable to the present invention is a sensor having a saturation charge number of 1,000,000 or more, preferably a saturation charge number of 3,200,000 or more, and particularly preferably a saturation charge number of 10,000,000 or more. Further, the sensor 13 applicable to the present invention has an SN ratio of 60 dB or more (corresponding to a saturation charge number of about 1,000,000 or more), particularly preferably 65 dB or more (corresponding to a saturation charge number of about 3,200,000 or more), and particularly preferably 70 dB or more (corresponding to a saturation charge number of about 10,000,000 or more). A sensor having a saturation charge number or an SN ratio satisfying the above conditions is suitable because it has a high SN ratio performance and can capture a minute difference in the amount of light under high illuminance.

It is preferable that the sensor 13 according to the present invention can clearly image a fluid moving in a living body (for example, blood cells in the blood) at a high frame rate. Since a sensor having a saturation charge number or an SN ratio satisfies the above conditions can increase a signal amount per frame, it is preferable, since even when the frame rate is increased (for example, 30 fps or more), it is possible to output a clear image that captures a minute difference in the amount of light under high illuminance, with the result that it becomes possible to measure biological information with high accuracy.

Further, in order to increase the signal amount in the sensor 13, it is also important to increase the light amount of the light source 11. Therefore, in addition to the sensor having a saturation charge number of 1,000,000 or more or a sensor having an SN ratio of 60 dB or more as described above, it is preferable to use a high output light source 11 capable of emitting a high amount of light corresponding to this sensor.

As the sensor 13 according to the present invention, it is preferable to apply a CMOS image sensor having a capacitor with a three-dimensional structure in the pixel and capable of accumulating light charges. The saturation charge number can be increased, by using a capacitor having a three-dimensional structure in the pixel. For the capacitor including the three-dimensional structure, for example, a silicon trench structure can be adopted, and further, the leakage current can be reduced by adopting a configuration in which the light charge is accumulated in the trench-embedded electrode node. However, the capacitor including the three-dimensional structure is not limited to the silicon trench structure, and a metal-insulating film-metal type capacitor having a three-dimensional structure formed in the wiring layer may be used.

As the sensor 13 according to the present invention, it is preferable to apply a CMOS image sensor provided with a deep p-well (DPW) so as to cover the region of the capacitor including the three-dimensional structure. By this configuration, it is possible to suppress the leakage current from the capacitor including the three-dimensional structure to the photodiode and to form a potential structure for drifting the optical charge generated in the deep portion of the photodiode to the photodiode.

As the sensor 13 according to the present invention, it is preferable to apply a CMOS image sensor having a capacitor having a uniform capacitance in a specific signal voltage range. The specific signal voltage range is preferably, for example, 0.5 to 3.0 V, and it is preferable that a linear response can be obtained with respect to the amount of light received in the specific signal voltage range.

As the sensor 13 according to the present invention, it is preferable to apply a CMOS image sensor having a photodiode quantum efficiency of 50% or more with respect to near-infrared light used in the present invention. By using a CMOS image sensor whose photodiode quantum efficiency satisfies the above conditions, the received near-infrared light is efficiently converted into electric charge, and high sensitivity to near-infrared light is realized. In order to improve the photodiode quantum efficiency, it is conceivable to stretch the depletion layer using a high resistance substrate, that is, to stretch the effective sensitivity region in the depth direction.

As the sensor 13 according to the present invention, it is preferable to apply a CMOS image sensor capable of applying an electric potential to a substrate to form an electric field in the depth direction of the substrate. As a result, it is possible to suppress crosstalk between pixels of signal charges (light charges) for near-infrared light having a large penetration length and improve the resolution of near-infrared light.

As the sensor 13 according to the present invention, it is preferable to apply a CMOS image sensor having a wide dynamic range. In the present invention, a measurement target location of the measurement target for biological information and a reference location different from the measurement target location are selected in the two-dimensional image. When the biological information of the measurement target is the blood glucose in the blood, the blood vessel site is selected as the measurement target location, and the non-vascular site is selected as the reference location. Normally, the blood vessel site is imaged darker than the non-vascular site, so if the amount of light is increased in order to image the blood vessel site brightly, so that there is a possibility that a phenomenon (blown out) that the non-vascular site becomes brighter and the non-vascular site becomes too bright and white, will occur. For this reason, a CMOS image sensor that can cover from bright areas to brighter areas, especially under high illuminance conditions is preferably applied, in order to image blood vessel site brightly and to image brighter non-vascular site without causing overexposure.

As the sensor 13 according to the present invention, it is preferable to apply a CMOS image sensor having 4000 or more pixels. By using a CMOS image sensor in which the number of pixels satisfies the above condition, a high-resolution image can be obtained, so that in the same image, a measurement target location (for example, a blood vessel site) and a reference location (for example, a non-vascular site) can be easily and surely identified.

Hereinafter, the features and usefulness of the biological information measurement device 10 according to the present invention will be described.

The biological information measurement device 10 according to the present invention can select a measurement target location and a reference location, further can use the information obtained from the reference location as a reference, and can acquire the biological information from the information obtained from the measurement target location.

In the technology disclosed in Patent Document 1, first, light is emitted from the entire light emitting portion to image the entire measurement target, then the locations of the blood vessel site and the non-vascular site are identified based on the obtained image for measurement, and the blood vessel pattern acquisition stage of determining the light emitting location, the light receiving location for measurement, and the light receiving location for reference is executed. Thereafter, the light is emitted only from the light emitting location for measurement by controlling the light emitting location in the light emitting portion, and the measurement stage to acquire the measured value at the blood vessel site and the measured value at the non-vascular site (reference) from the amount of light received at the light receiving location for measurement and the light receiving location for reference is performed.

In the disclosed technology of Patent Document 1, a blood vessel pattern acquisition stage and a measurement stage are provided, and light emission and light reception are performed at each stage. In particular, in the blood vessel pattern acquisition stage, light is emitted from the entire light emitting portion, and in the measurement stage, light is emitted only at the measurement light emitting location. For this reason, there is a problem that the time until the measurement result is obtained becomes long, and there is a problem that the reference accuracy and the measurement accuracy are impaired due to the positional deviation of the blood vessel site and the non-vascular site due to the movement of the subject.

In comparison with the disclosed technology of Patent Document 1, the biological information measurement device 10 according to the present invention is configured to be able to acquire the image information that enables the both of identification of the location of the blood vessel site and the non-vascular site and acquisition of the measurement value of each of the blood vessel site and the non-vascular site, by one light emission and light reception, without providing a plurality of stages of blood vessel pattern acquisition stage and measurement stage. This means that the biological information measurement device 10 according to the present invention is advantageous in comparison with the disclosed technology of Patent Document 1, in the point that the measurement result can be obtained in a shorter time and in the point that the measurement is less affected by misalignment due to the movement of the subject. It should be noted that in the present specification, one-time light emission and light reception means that the light emission state in the light source and the light reception state in the sensor are fixed to predetermined states, for example, the light emission position in the light source and the light reception position in the sensor are not changed. The disclosed technology of Patent Document 1 emits light from the entire light emitting portion at the blood vessel pattern acquisition stage, and emits light only from the measurement light emitting position at the measurement stage, and does not perform one-time light emission and light reception.

In the disclosed technology of Patent Document 1, when it is attempted to identify the position of the blood vessel site and non-vascular site and to obtain measured values of blood vessel site and non-vascular site by one light emission and light reception without providing a plurality of stages, since the blood vessel site absorbs light by the blood, the amount of transmitted light received by the sensor becomes small, so that the image is darkened. If the amount of transmitted light at the blood vessel site is too small, which means too dark, the sensor amount of light may fall below the lower limit of the amount of light that can be received by the sensor. As a result, it is anticipated that the location of the blood vessel site and the light transmittance at the blood vessel site cannot be detected correctly.

As a measure to prevent the blood vessel site from becoming too dark, it is conceivable to increase the amount of light emitted from the light source to compensate for the decrease in the amount of received light due to the absorption of the blood vessel site. However, in this case, while the blood vessel site will be brighter, the amount of transmitted light in non-vascular site will be greater, resulting in a brighter image. If the amount of transmitted light in the non-vascular area is too large, which means, too bright, the amount of light may exceed the upper limit of the amount of light that can be received by the sensor. As a result, it is anticipated that the light transmittance in the non-vascular site cannot be detected correctly.

In view of the problems anticipated as described above, the biological information measurement device 10 according to the present invention is characterized by having a sensor having a saturation charge number of 1,000,000 or more. The biological information measurement device 10 according to the present invention can take image of the measurement target location (for example, a blood vessel site) clearly and brightly by capturing high-intensity light using a sensor having a saturation charge number of 1,000,000 or more, and can take image of the reference location (for example, non-vascular site) that are brighter than the measurement target location without causing overexposure. This makes it possible to acquire the biological information by one light emission and light reception without providing a plurality of stages for changing the light emission position in the light emitting portion and the light reception position in the light receiving portion. More specifically, it becomes possible to select both of the measurement target location and the reference location from the image information obtained by using the sensor having a saturation charge number of 1,000,000 or more by one light emission and light reception, and further, it is possible to acquire the measured value from the measurement target location and acquire the reference from the reference location. In order to capture high illuminance light using a sensor having a saturation charge number of 1,000,000 or more, it is preferable to irradiate a living body with a high amount of light using a high output light source.

Figure 5:
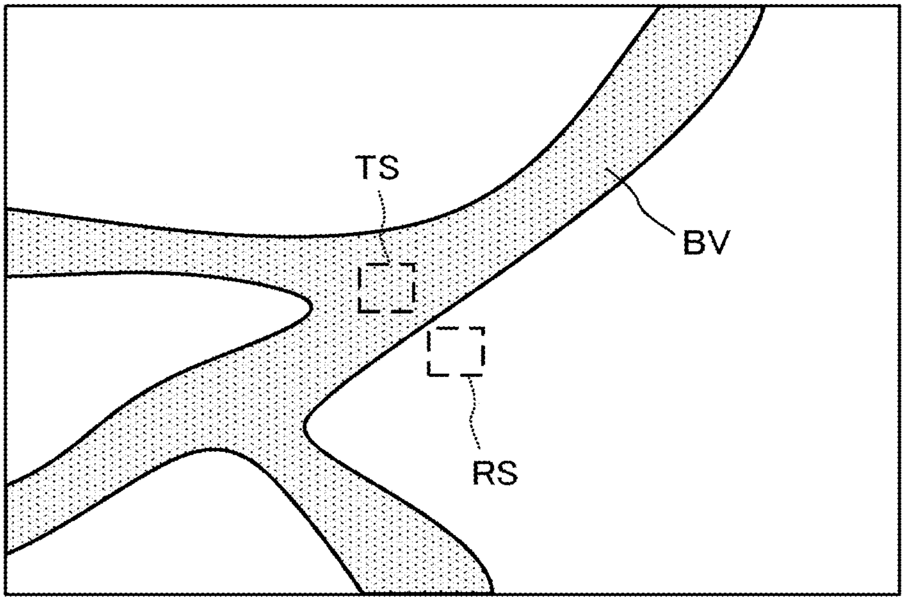
FIG. 5 is a diagram schematically showing an example of image information obtained by the biological information measurement device according to the present invention.

Hereinafter, the measurement target locations and reference locations will be described. FIG. 5 is a diagram schematically showing an example of image information obtained by the biological information measurement device 10 according to the present invention. FIG. 5 shows an image of a blood vessel BV used when measuring a blood glucose as biological information.

In the captured image shown in FIG. 5, the blood vessel BV is imaged. The blood vessel BV is imaged darker than the location where the blood vessel BV does not exist. As described above, the biological information measurement device 10 according to the present invention has a sensor having a saturation charge number of 1,000,000 or more, images a blood vessel BV brightly and clearly, and a location where the blood vessel BV does not exist can be imaged without causing overexposure.

As shown in FIG. 5, the specific location selection unit **14*a*** selects the location where the blood vessel BV exists as the measurement target location TS, and selects the location where the blood vessel BV does not exist as the reference location RS. A sensor having a saturation charge number of 1,000,000 or more can accurately capture the amount of light received at the measurement target location TS and the amount of light received at the reference location RS.

The light received at the measurement target location TS is affected not only by the absorption of light by blood in the blood vessel BV, but also by the absorption of light by cells and body fluids existing around the blood vessel BV. On the other hand, the light received at the reference location RS reflects only the influence of light absorption by cells, body fluids, and the like existing around the blood vessel BV. Therefore, by correcting the light receiving amount at the measurement target location TS using the light receiving amount at the reference location RS, it is possible to eliminate the influence of light absorption by cells, body fluids, and the like, superimposed on the light receiving amount at the measurement target location TS. As a result, only the influence of the absorption of light by the blood in the blood vessel BV can be extracted, so that the blood glucose in the blood can be measured accurately.

Figure 6:
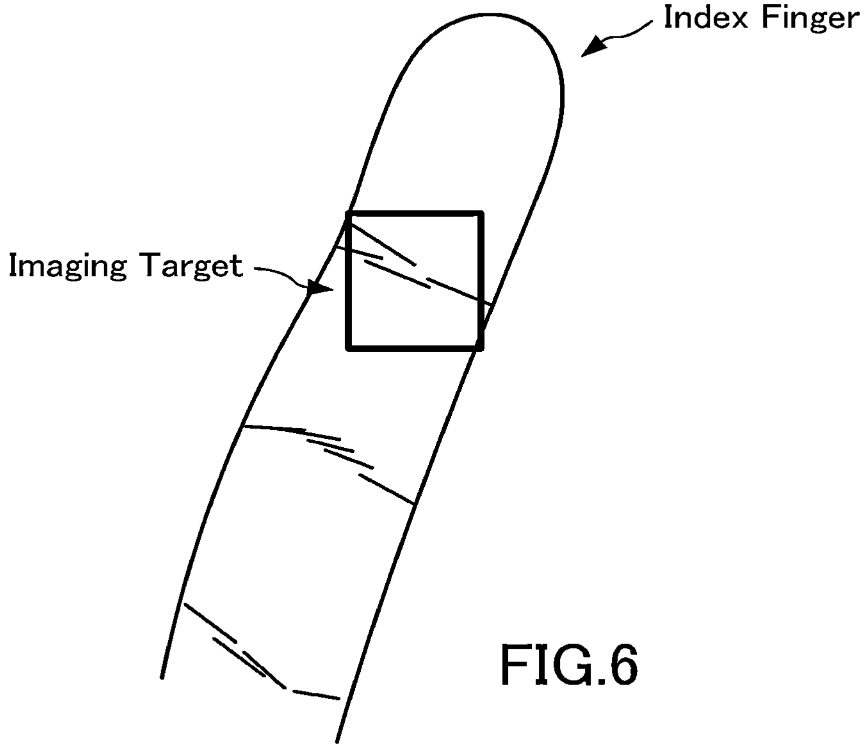
FIG. 6 is a diagram showing a finger joint portion selected as a blood vessel imaging target in relation to the biological information measurement device according to the present invention.
Figure 7:
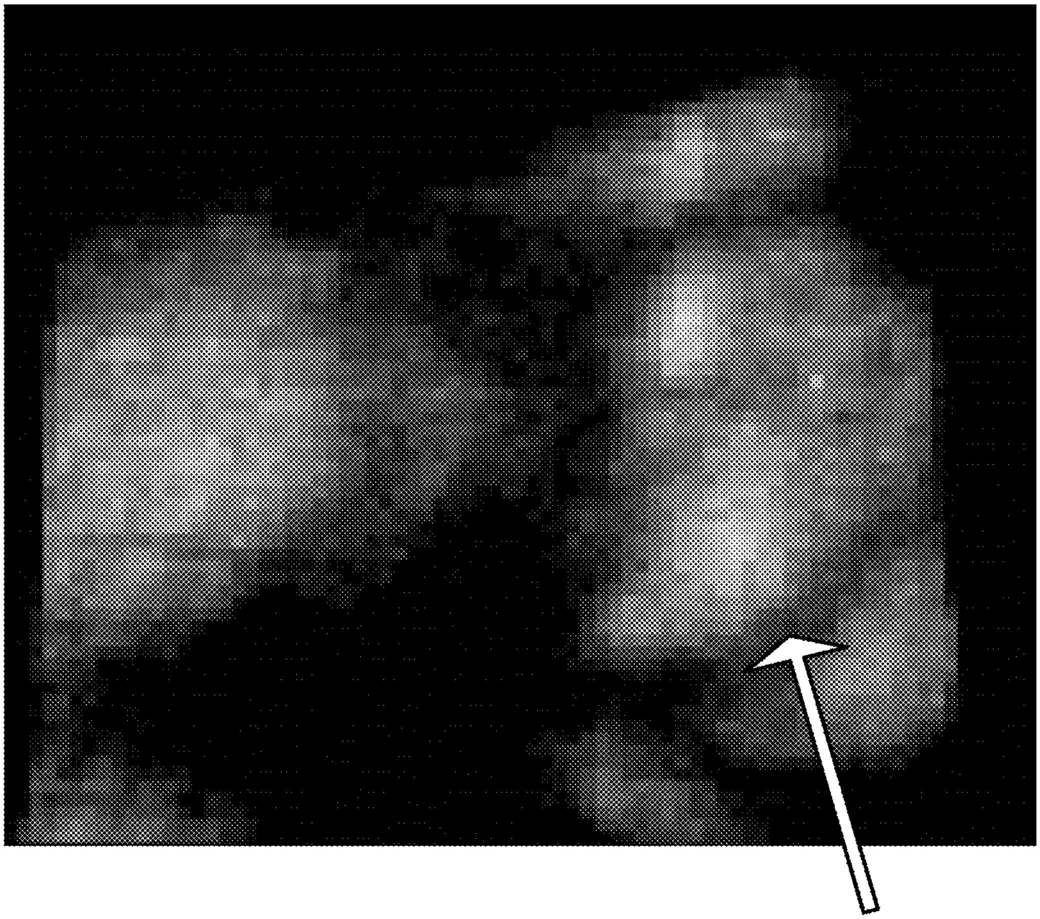
FIG. 7 is a captured image of the finger joint portion shown in FIG. 6.

Further, the present inventors selected a finger joint portion using a sensor having a saturation charge number of 1,000,000 or more, and imaged a blood vessel with transmitted light. The imaged finger joint portion is the first joint portion on the ventral side of the index finger shown in FIG. 6. FIG. 7 shows the captured image.

As described above, the present invention makes it possible to irradiate a living body with light, to receive light by an image sensor that has a plurality of pixels arranged in an array in a two-dimensional plane and has a saturation charge number of 1,000,000 or more to transmit, reflected, or scattered light in a living body, to select the measurement target location of the measurement target or biological information and the reference location different from the measurement target location based on the amount of light received, and to acquire the biological information from the information at the measurement target location by using the information at the reference location as a reference. Therefore, the present invention can be applied to a technology for non-invasively measuring biological information in the living body using light.

The embodiments described above are described for facilitating the understanding of the present invention, and are not described for limiting the present invention. Therefore, each element disclosed in the above-described embodiment is intended to include all design changes and equivalents belonging to the technical scope of the present invention.

EXPLANATION OF REFERENCE NUMERALS

10 Biological Information Measurement Device
11 Light Source
11*a* Optical Element
12 Filter
13 Sensor
14 Signal Processing Unit
14*a* Specific Location Selection Unit
14*b* Biological Information Acquisition Unit
15 Display Unit
16 Data Storage Unit
17 Operation Unit
18 Control Unit
101 Pixel Array Unit
102 Reading Unit
103 Pixel Train Output Signal Line
104 Current Source
105 Pixel
BV Blood Vessel
RS Reference Location
S Subject
TS Measurement Target Location

What is claimed is:

1. A biological information measurement device, comprising:

a light source that irradiates light;

an image sensor that receives the light irradiated from the light source transmitted, reflected or scattered in a living body, outputs information according to an amount of the received light, has a plurality of pixels arranged in an array in a two-dimensional plane, and has a saturation charge number of 1,000,000 or more, and outputs information forming a single two-dimensional image;

specific location selection circuitry that, in the single two-dimensional image formed from the information obtained by the image sensor, selects a measurement target location including a measurement target of the biological information, and selects a reference location different from the measurement target location that does not include the measurement target of the biological information; and biological information acquisition circuitry that acquires the biological information from information at the measurement target location selected in the single two-dimensional image, by using, as a reference, information at the reference location selected in the single two-dimensional image.

2. The biological information measurement device according to claim 1, wherein an SN ratio of the image sensor is 60 dB or more.

3. The biological information measurement device according to claim 2, wherein the light source is a surface emitting type light emitting diode.

4. The biological information measurement device according to claim 2, wherein an optical element having a transverse mode conversion function is arranged between the light source and the image sensor.

5. The biological information measurement device according claim 2, wherein the measurement target location is a location including a blood vessel in the living body, and the reference location is a location not including the blood vessel in the living body.

6. The biological information measurement device according to claim 2, wherein the biological information is blood glucose in blood in the living body.

7. The biological information measurement device according to claim 1, wherein the light source is a surface emitting type light emitting diode.

8. The biological information measurement device according to claim 7, wherein an in-plane variation of the surface emitting type light emitting diode is 10% or less.

9. The biological information measurement device according to claim 7, wherein an optical element having a transverse mode conversion function is arranged between the light source and the image sensor.

10. The biological information measurement device according claim 7, wherein the measurement target location is a location including a blood vessel in the living body, and the reference location is a location not including the blood vessel in the living body.

11. The biological information measurement device according to claim 7, wherein the biological information is blood glucose in blood in the living body.

12. The biological information measurement device according to claim 1, wherein an optical element having a transverse mode conversion function is arranged between the light source and the image sensor.

13. The biological information measurement device according to claim 12, wherein the optical element is an aspherical lens.

14. The biological information measurement device according to claim 12, wherein the optical element is a diffractive optical element.

15. The biological information measurement device according to claim 12, wherein the optical element is a parallel flat plate of quartz.

16. The biological information measurement device according claim 1, wherein the measurement target location is a location including a blood vessel in the living body, and the reference location is a location not including the blood vessel in the living body.

17. The biological information measurement device according to claim 1, wherein the biological information is blood glucose in blood in the living body.

* * * * *